(12) United States Patent
Shioda et al.

(10) Patent No.: US 7,904,206 B2
(45) Date of Patent: Mar. 8, 2011

(54) METHOD AND APPARATUS FOR REMOVABLY HOLDING MEDICAL DEVICE

(75) Inventors: Keiji Shioda, Tokyo (JP); Satoshi Otsuka, Tokyo (JP); Masaaki Ueda, Sagamihara (JP); Kazuhito Nakanishi, Tokyo (JP)

(73) Assignee: Olympus Corporation (JP)

( * ) Notice: Subject to any disclaimer, the term of this patent is extended or adjusted under 35 U.S.C. 154(b) by 1597 days.

(21) Appl. No.: 11/042,945

(22) Filed: Jan. 24, 2005

(65) Prior Publication Data

US 2005/0165271 A1 Jul. 28, 2005

(30) Foreign Application Priority Data

Jan. 23, 2004 (JP) ................................ 2004-015671

(51) Int. Cl.
G05B 19/18 (2006.01)
G05B 19/04 (2006.01)

(52) U.S. Cl. .......... 700/250; 700/245; 700/257; 700/264

(58) Field of Classification Search ........................ None
See application file for complete search history.

(56) References Cited

U.S. PATENT DOCUMENTS

| | | | | |
|---|---|---|---|---|
| 4,661,797 | A | * | 4/1987 | Schmall ........................ 340/561 |
| 5,115,179 | A | * | 5/1992 | Fujii et al. ................. 318/568.13 |
| 6,120,433 | A | * | 9/2000 | Mizuno et al. ................. 600/102 |
| 6,166,504 | A | * | 12/2000 | Iida et al. ...................... 318/560 |
| 6,866,671 | B2 | * | 3/2005 | Tierney et al. ................. 606/130 |
| 2003/0109780 | A1 | * | 6/2003 | Coste-Maniere et al. ..... 600/407 |
| 2004/0133189 | A1 | * | 7/2004 | Sakurai ............................ 606/1 |

FOREIGN PATENT DOCUMENTS

| | | |
|---|---|---|
| EP | 0 587 948 A1 | 3/1994 |
| EP | 0 752 237 A1 | 9/1995 |
| EP | 1 103 223 A2 | 5/2001 |
| JP | 2002-345831 | 12/2002 |

OTHER PUBLICATIONS

Letter from Spanish associate commenting on enclosure of Search Report issued on Apr. 1, 2005 in connection with corresponding application No. EP 05 00 1238.
Search Report issued by European Patent Office on Apr. 1, 2005 in connection with corresponding application No. EP 05 00 1238.

* cited by examiner

*Primary Examiner* — Khoi Tran
*Assistant Examiner* — Bhavesh V Amin
(74) *Attorney, Agent, or Firm* — Ostolenk Faber LLP (57) ABSTRACT

An apparatus for holding a medical device has an arm unit equipped with, for example, a polyarticular arm, which holds the medical device such as endoscope movably in the space. Additionally to a determination unit and a controller, the holding apparatus has an operation unit equipped with a plurality of operation members with which an operator's operation causes the arm unit to be moved spatially. The determination unit determines whether or not operator's operations at the plurality of operation members corresponds to an improper state deviating from a properly operated state in which at least two predetermined operation members have been operated within a predetermined period of time which is set to measure simultaneity for operations. If it is determined that the operation is in the improper state, the controller prohibits the arm unit from moving. As long as the operation is proper, the arm unit can be moved.

28 Claims, 11 Drawing Sheets

METHOD AND APPARATUS FOR REMOVABLY HOLDING MEDICAL DEVICE

CROSS REFERENCES TO RELATED APPLICATIONS

The present application relates to and incorporates by reference Japanese Patent application No. 2004-015671 filed on Jan. 23, 2004.

BACKGROUND OF THE INVENTION

1. Technical Field of the Invention

The present invention relates to a method and apparatus for removably holding various medical devices such as endoscopes used, for example, during surgical operations in cranial nerve surgery.

2. Related Art

An apparatus for holding medical devices (medical-device holding apparatus) has been known, which has a polyarticular arm equipped with a holder that holds medical devices and joints equipped with brakes to selectively lock/unlock the turns of the arm. This medical-device supporting apparatus allows the holder to support, for example, an endoscope so that the endoscope is positioned to face a desired portion to be examined of a patient. In this attitude of the holder, the joints are locked to prevent a field of view of the endoscope from deviating outside the portion to be examined. Thus a surgeon is able to concentrate on the surgical operation, without being bothered by positional adjustment operations of the endoscope.

Meanwhile, as described in Japanese Patent Publication (unexamined) No. 2002-345831, the medical-device holding apparatus has a grasping member which is used to move the holder (i.e., the endoscope), wherein the grasping member is arranged close to the holder. That is, in order to lock and unlock the brakes in the joints, the grasping member is arranged to substantially be perpendicular to an insertion axis assigned to the endoscope and is equipped two operation switches secured thereon. Thus a surgeon grasps the grasping member and, at the same time, pushes those two operation switches by, usually, the first and middle fingers. This push operation allows the brakes to be activated, so that each joint is released from being locked. In other words, in the condition where both the two operation switches are not pressed at the same time (, or together), each joint will not be released from being fixed. It is therefore possible for a surgeon to worry about erroneous release operations of the brakes during a surgical operation, so that the surgeon can concentrate on the operation.

Further, in operating the medical-device holding apparatus, it is required that a surgeon's touch to the arm will not move the arm under the condition in which the brakes have been locked in the joints. To realize such a situation, a large amount of fixing force should be given to each brake. In contrast, with the arm made free (i.e., the locks are released), it should be constructed such that a medical device that has been held by the apparatus can be moved freely with a light amount of operator's force. In addition, with taking malfunctions and others of the joints, design is made such that the brakes sustain a certain specific level of braking force to prevent the arm from moving in such malfunction cases.

SUMMARY OF THE INVENTION

Accordingly, an object of the present invention is to provide a method and apparatus holding a medical device, which has the capability of selectively locking and unlocking the joints of an arm unit holding the medical device in a proper manner.

As one aspect, the present invention provides an apparatus for holding a medical device, comprising: an arm unit spatially movably holding a single medical device; an operation unit equipped with a plurality of operation members to be operated by an operator to enable the arm unit to move spatially; a determination unit determining whether or not an operator's operation at the plurality of operation members corresponds to an improper state deviating from a properly operated state in which at least two operation members of the operation members have been operated within a predetermined period of time; and a movement controller prohibiting, in a controlled manner, a spatial movement of the arm unit when the determination unit determines that the operation at the plurality of operation members corresponds to the improper state.

For making the arm unit holding the medical device movable, it is required for an operator to operate at least two predetermined operation members among a plurality of operation members secured on an operation unit. Only when a properly operated state is established where the "at least two operation members" are operated within a predetermined period of time (for example, a few seconds), the operator is allowed to move the arm unit, so that the arm unit can be moved to spatially move the medical device such as endoscope at operator's will.

However, the operator's operation is in the improper state deviating from the "properly operated state," the arm unit is not allowed to move. In other words, the medical device is not allowed to move spatially; of course, cannot be moved at operator's will. Hence the medical device is obliged to keep its locked (fixed) state at the same spatial position. The "improper state" includes an "improperly operated state," in which an operator has not operated the foregoing "at least two operation members" within a predetermined period of time; an "accidentally operated state," in which only part of the foregoing "at least two operation members" is operated due to, for example, a push from any obstacle; and a "malfunctioning state," in which a signal resulting from operational failures of the operation unit is outputted from the operation unit, the signal showing a situation where only part of the foregoing "at least two operation members" is operated. Incidentally, though the states deviating from the "properly operated state" includes a "non-operated state," but this is omitted from the explanations in the present invention, because such a state does not relate to the movement of the arm unit any longer.

As another aspect of the present invention, there is provided an apparatus for holding a medical device, comprising: an arm unit spatially holding the medical device; an electric driver spatially moving the medical device and being secured to the arm unit; an operation unit equipped with a plurality of operation members to be operated by an operator to control a spatial movement of the medical device; a determination unit determining whether or not an operator's operation at the plurality of operation members corresponds to an improper state deviating from a properly operated state in which at least two operation members of the operation members have been operated within a predetermined period of time; and an electric operation controller prohibiting the electric driver from being operated in a controlled manner, in cases where it is determined by the determination unit that the operation is in the improper state. Hence the improper states (i.e., the improperly operated state, accidentally operated state, and malfunctioning state) are found to prohibit the operations of the electronic driver, resulting in that the medical device is locked from its spatial movement.

Still, as another aspect of the present invention, there is provided a method for holding a medical device to be spatially movable, the medical device being held by an arm unit by allowing an operator to operate a plurality of operation members, the method comprising steps of: determining whether or not an operator's operation at the plurality of operation members corresponds to an improper state deviating from a properly operated state in which at least two operation members of the operation members have been operated within a predetermined period of time; and prohibiting, in a controlled manner, a spatial movement of the arm unit when it is determined that the operation at the plurality of operation members corresponds to the improper state. This holding method also copes with the forgoing improper states in the same way as the above.

DETAILED DESCRIPTION OF THE PREFERRED EMBODIMENTS

Various embodiments of medical-device holding apparatuses according to the present invention will now be described with reference to the accompanying drawings.

First Embodiment

Referring to FIGS. 1-5, a medical-device holding apparatus according to a first embodiment will now be described.

Figure 1:
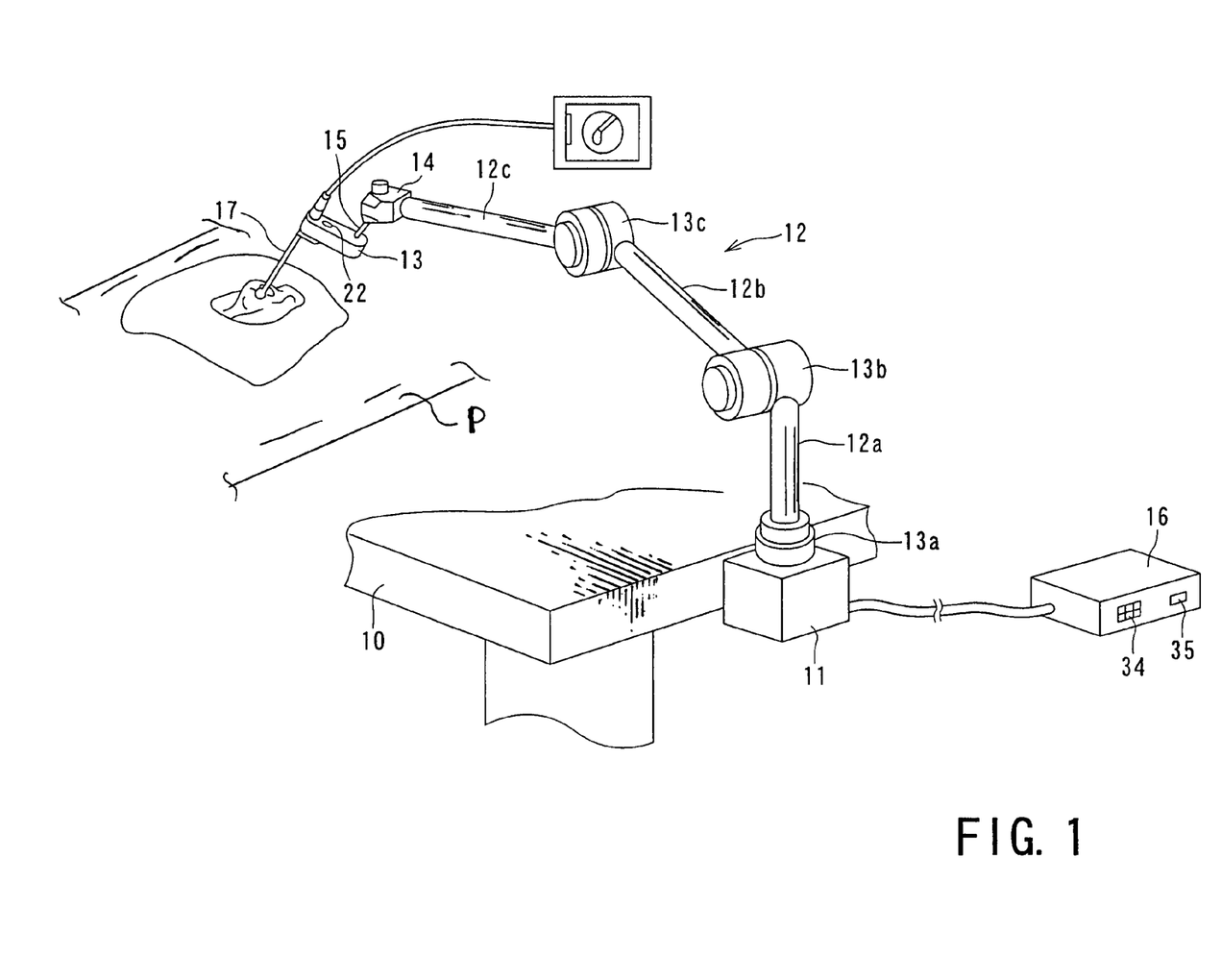
FIG. 1 is a perspective view showing the configuration of a medical-device holding apparatus according to a first embodiment of the present invention.

As shown in FIG. 1, the medical-device holding apparatus is provided with a support base 11, a polyarticular arm 12 whose one end is attached to the support base 11, and a holder 13 sustained at the other end of the polyarticular arm 12.

The support base 10 is detachably attached to an attaching member, such as floor or patient bed. The polyarticular 12 is provided with three arms consisting of first to third arms 12a-12c, three joints 13a-13c arranged at one end of the first arm 12a, between the first and second arms 12a and 12b, and between the second and third arms 12b and 12c, respectively, and a ball joint attached to the top of the third arm 12c. Therefore, on the support base 10, the arms 12a, 12b, and 12c are connected to each other in this order so that the arms 12a-12c can be moved rotatably in the three-dimensional space via the joints 13a, 13b, and 13c. In addition, a pillar 15 is suspended from the ball joint 14 attached to the headmost arm 12c, and a holder 13 to which a medical device is held is secured to the pillar 15.

The ball joint 14 incorporates a known fluid clutch 28d (refer to FIG. 3) that uses fluid, such as air, as a pressure transmission medium. The fluid clutch 28d is electrically connected to a control box 16 composing as control means and responds to a command from the control box 16 in such a manner that a clutch portion (i.e. a brake not shown) of the fluid clutch 28d are selectively controlled between two states of being clutched and non-clutched. The clutch portion connects both the pillar 15 (that is, the holder 13) and the third arm 12c. Thus, when the clutch portion is in its clutched state, the pillar 15 (holder 13) is positionally fixed to the third arm 12c (i.e., positionally fixed). In contrast, in cases where the clutch portion is in its non-clutched state, the pillar 15 (i.e., the holder 13) will not be positionally fixed to the third arm 12c, and can be moved freely. To be short, the fluid clutch 28d responds to the existence and non-existence of fluid pressure to be supplied so that the holder 13 is positionally fixed to the ball joint 14 or positionally released from being fixed to the ball joint 14 in a selective manner.

As described, the holder 13 is coupled with the third arm 12c via the ball joint 14 with the fluid clutch 28d, and can be rotated and moved with suspending from the third arm 12c under the fluid clutch 28d is unclutched (i.e., released).

The fluid clutches 28a-28c (refer to FIG. 3) employing fluid such as air and having the similar construction and function are incorporated in the joints 13a-13c, respectively, and can selectively be switched between their clutched or non-clutched states in answer to a control signal from the control box 16. The fluid clutches 28a-28c are constructed to release the clutch portion in response to an application of pressure. In such a control manner, the first arm 12a is able to selectively realize the position-fixed state or position-free state to the support base 11, the second arm 12b to the first arm 12a, and the third arm 12c to the second arm 12b.

Figure 2:
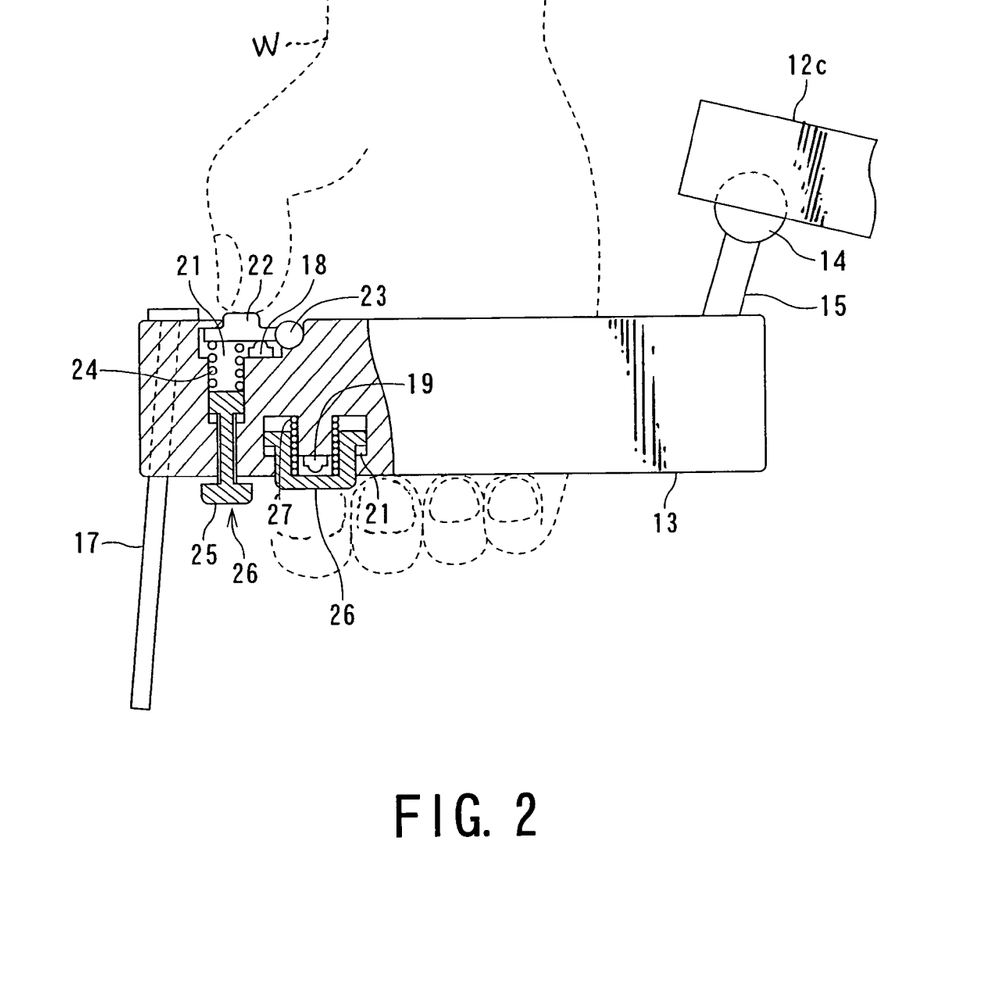
FIG. 2 is a side view, partly sectioned, showing a holder employed by the holding apparatus in the first embodiment.

On the headmost end of the holder 13, as shown in FIGS. 1 and 2, an endoscope 17 serving as one of medical devices to treat and observe the inside of a patient to be examined is detachably loaded and supported. In FIG. 1, a reference P depicts a patient to be observed and treated and by the endoscope 17.

By way of example, the holder 13 is formed into a cuboid-like member having a specific thickness and a section perpendicular to its longitudinal axis formed into a rectangle. This holder 13, which can be grasped by a user, has switches loaded thereto which can be operated by the user. The size of the cuboid-like member is set to an appropriate amount which makes it possible that the user grasps the member well.

On a base-side end of the holder 13, one end of the foregoing pillar 15 is secured, while at the head-side end, a loading hole is formed therethrough. The endoscope 17 is loaded in the loading hole in a detachable manner.

On upper and lower surfaces of the holder 13 are formed a first switch and a second switch 18 and 19, which serve as input means of operation signals, consist of microswitches, respectively. The upper and lower surfaces are defined as upward and downward surfaces of the holder 13 when an operator can grasp the holder 13 from a direction which makes the endoscope 17 downward, as shown by a chain double-dashed line W in FIG. 2.

The first and second switches 18 and 19 are formed to provide switch signals to the control box 16 through lead wires respectively connecting to the control box 16. As will be described later, the control box 16 has the configuration that uses the switch signals to produce control signals in which the states indicated by the switch signals are reflected, the control signals being fed to the fluid clutch 28d of the ball joint 14 and the fluid clutches 28a-28c of the joints 13a-13c.

The structures of the first and second switches 18 and 19 will now be described. As illustrated in FIG. 2, the first and second switches 18 and 19 are embedded in two locations of the holder 13; to be specific, when a user grasps the holder 13, one switch 18 is located close to the holder near to an endoscope-loading region of the holder 13, that is, a head-side given position of the holder 13 to which the thumb is approximately touched on the upper surface and the other switch 19 is located at a given position of the holder 13 to which the first finger is approximately touched on the lower surface. The first switch 18 is embedded to have its operating portion opened from the upper surface, whilst the second switch 19 is embedded to have its operating portion opened from the lower surface.

More specifically, a first and second concave switch accommodating rooms 20 and 21 are formed at given positions of the holder 13, which are close to the head thereof. These accommodating rooms 20 and 21 are formed to provide their main opening opened from the upper and lower surfaces of the holder 13, but are slightly positionally shifted with each other in a longitudinal direction of the holder 13. In the first and second concave switch accommodating rooms 20 and 21, the first and second switches 18 and 19 are accommodated with their operating directions upside down with each other. Specifically, in FIG. 2, the operating direction to the first switch 18 is a downward direction and that to the second switch 19 is an upward direction. The lead wires of the fist and second switches 18 and 19 are electrically coupled to the control box 16, respectively.

Of the above switch accommodating rooms 20 and 21, the first switch accommodating room 20 accommodates the first switch 18 together with a switch lever 22 and a hinge 23, where the switch lever 22 faces the first switch 18 to freely rotate thanks to the hinge 23. To the switch lever 22 is provided a pushing force via a first spring member 24 in the clockwise in FIG. 2 (corresponding to a direction that turns the first switch 18 "on"). This first spring member 24 has a base portion engaging with a tip of an operation-force-amount adjusting member 25 in an adjustable fashion. This adjusting member 25 has a middle portion held by holder 13 in a screw-adjustable manner and a base portion to which an operating portion 26 is secured so that the operating portion 26 can be operated. The operating portion 26 is located to protrude from the lower surface of the holder 13. Accordingly, rotating the adjusting member 25 makes the adjusting member 25 itself advance against the first spring member 24, whereby the pushing force of this first spring member 24 can be adjusted. An amount of force required to operate the switch lever 22 can be adjusted.

Figure 3:
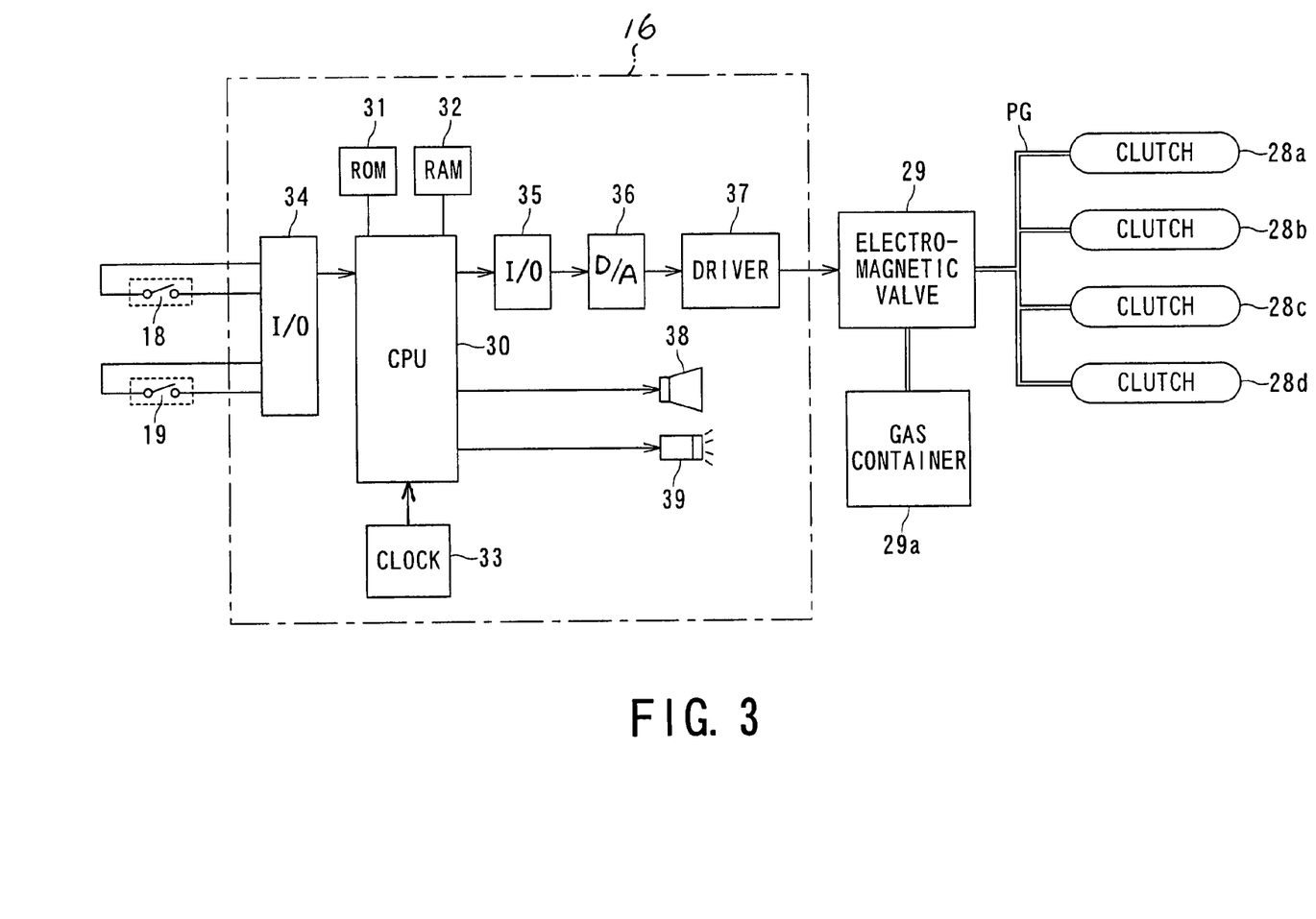
FIG. 3 is a block diagram of hardware elements of a controller employed by the holding apparatus in the first embodiment.

As shown in FIG. 3, each of the foregoing fluid clutches 28a-28d is coupled with an electromagnetic valve 29 via a duct PG. The electromagnetic valve 29 is coupled with a fluid-pressure source 29a, which is for example a gas container placed in an operation room. Hence, responsively to the open and close of the electromagnetic valve 29, the fluid of a given pressure (e.g., air) is supplied to the fluid clutches 28a-28d, respectively, from the fluid-pressure source 29a.

As shown in FIG. 3, the control box 16 is provided with a CPU 30, in which processing on software executed by the CPU 30 provides desired calculation functions. The calculation part of the control box 16, however, is not always limited to the computer configuration that uses the CPU, but may be configured into a hardware construction that provides desired functions using logic circuits such as AND and OR circuits.

The control box 16 according to the present embodiment is provided with, besides the CPU 30, peripheral devices including a ROM 31, RAM 32, clock circuit 33, input interface 34, and output interface 35, a D/A converter 36 connected to the output interface 35, and a driver 37. In the ROM 31, programs are stored in advance, which are computer-readable and define procedures of calculation for control of the clutches which will be described later. When the CPU 30 is activated, it therefore reads in the programs from the ROM 31, and executes calculation in sequence based on the procedures defined by the read-in programs. The RAM 32 is a memory temporarily used during the calculation of the CPU 30. The clock circuit 33 is placed to provide a reference clock signal to the CPU 30.

Connected to the input interface 34 are the first and second switches 18 and 19, so that on/off information from the switches 18 and 19 is transmitted to the CPU 30. A control signal produced through the calculation executed by the CPU 30 is sent to the D/A converter 36 via the output interface 35, thereby being subject to D/A conversion. The resultant control signal is amplified by the driver 37, and then supplied to the electromagnetic valve 29.

The control box 16 is also provided with, as information means, a buzzer 38 and an LED 39, which are connected to the CPU 30.

Figure 4:
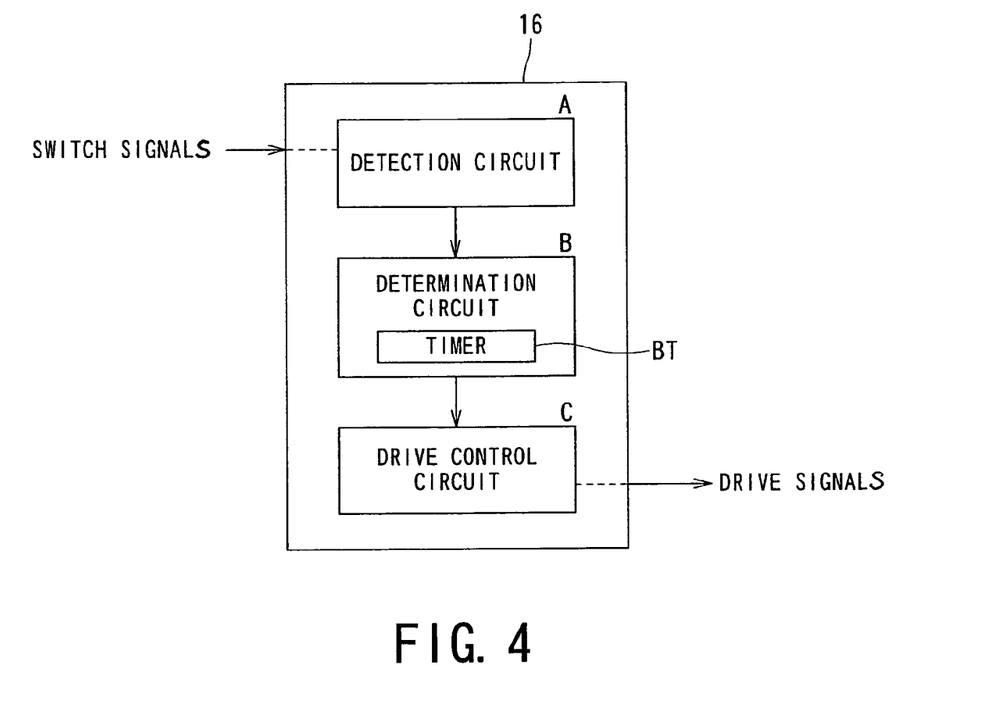
FIG. 4 is a functional block diagram of the controller employed by the holding apparatus in the first embodiment.

Calculating functions realized by the CPU 30 can be depicted as shown in FIG. 4. Concretely, with its software processing, the CPU 30 is able to present the functions for a switch detection circuit "A," determination circuit "B," and drive/control circuit "C."

Of these functions, the switch detection circuit "A" detects the on/off states of the first and second switches 18 and 19, and operates on the basis of the detected results such that it outputs an "on" signal to the drive/control circuit "C," only when both the first and second switches 18 and 19 are turned "on" almost simultaneously (that is, at the same time or within a predetermined period of time). Responsively to the "on" signal, the drive/control circuit "C" outputs a drive signal to open the electromagnetic valve 29. When the electromagnetic valve 29 is opened, fluid pressure is applied from the fluid-pressure source 29a to the fluid clutches 28a, 28b, 28c and 28d, thus releasing the fluid clutches 28a-28d. As a result, the joints 13a-13c and boll joint 14 presents their position-free states, that is, released states from their position-fixed states.

Meanwhile, in cases where, of the first and second switches 18 and 19, either one switch is turned "on" over a predetermined period of time or more, the determination circuit "B" determines that either one switch has been pressed alone, and provides no control signal with the drive/control circuit "C" (i.e., "off" state). That is, the electromagnetic valve 29 becomes its closed sate or keeps its closed state. In this closed state of the electromagnetic valve 29, no fluid pressure is applied from the fluid-pressure source 29a to the fluid clutches 28a-28d, with the result that fluid clutches 28a-28d are kept clutched, whereby the joints 13a-13c are kept locked (i.e., in their position-fixed states).

The determination circuit "B" has a timer function (realized by a timer BT in FIG. 4) in order to measure a state where either the first or second switch 18 or 19 solely becomes "on" over a predetermined period of time or more.

Figure 5:
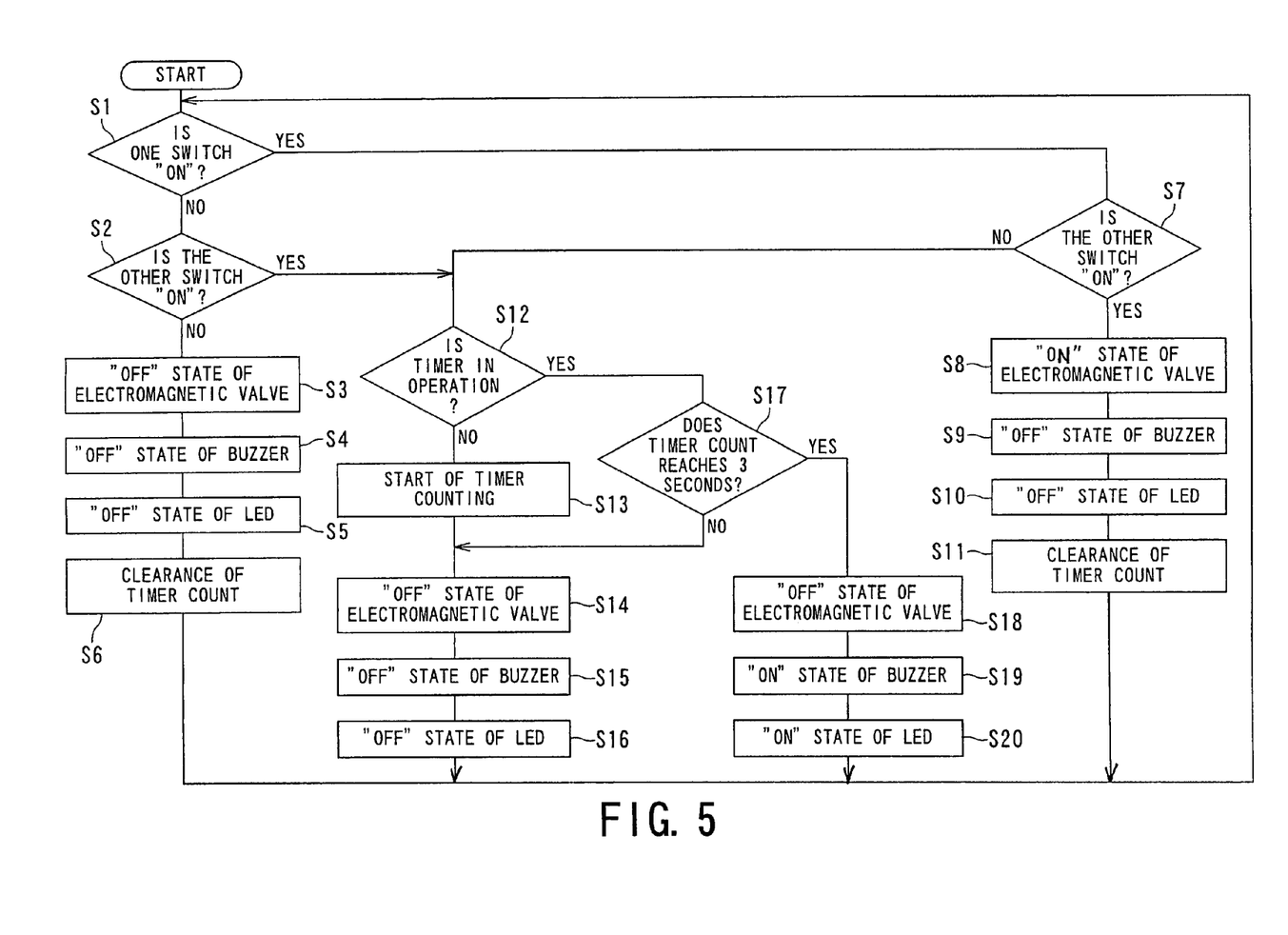
FIG. 5 is a flowchart showing the operations of the controller.

Referring to FIG. 5, practical procedures of calculation on the software processing executed by the CPU 30 will now be described.

The CPU 30 determines, at step S1, whether or not the first switch 18 is in the "on" state. If the determination is NO (that is, the first switch 18 is in the "off" state), the processing in the CPU 30 proceeds to step S2, whereat the CPU 30 determines whether or not the second switch 19 is in the "on" state. When the determination is NO (that is, the second switch 19 is in the "off" state), the CPU 30 makes the processing to proceed to step S3, where the CPU 30 commands the electromagnetic valve 29 to be or kept "off." The processing is then made to advance to steps S4-S6 in sequence, where the CPU 30 commands the buzzer 38 to be or kept "off" (step S4), commands the LED 39 to be or kept "off" (step S5), and commands the timer BT to initialize its count (step S6). Then the processing returns to step S2.

In addition, when it is determined "YES" at step S1, the CPU30 makes the processing to step S7, whereat it is further determined whether or not the second switch 19 is in the "on" state. If the determination at step S7 is "YES," the processing is shifted to step S8 to allow the electromagnetic valve 29 to be or kept "on." The processing is then made to advance to steps S9-S11 in sequence, where the CPU 30 commands the buzzer 38 to be or kept "off" (step S9), commands the LED 39 to be or kept "off" (step S10), and commands the timer BT to initialize its count (step S11). Then the processing returns to step S2.

Moreover, in cases where it is determined "yes" at step S2 or "no" at step S7, the processing in the CPU30 is shifted to step S12, where it is determined whether or not the timer BT is in operation. The determination at step S12 reveals the timer BT is not in operation (NO), the processing is shifted to step S13 to cause the timer BT to start its count operation. The processing at step S14 is then executed to allow the electromagnetic valve 29 to be "off." Further, at step S15, the buzzer 38 is made or kept "off," and then, at step S16, the LED 39 is made or kept "off," before returning to step S1.

In the case that the determination at step S12 is YES, that is, it is determined at step S12 if the timer BT is in operation or not, the CPU 30 shifts its operation to step S17, where it is determined if or not the timer BT has counted a predetermined period of time (for example, 3 seconds) or more. If YES at step S17, the processing at steps S18, S19, and S20 is executed in turn. Specifically, the electromagnetic valve 29 is brought into or kept "off" (step S18), the buzzer 38 is turned or kept "on" (step S19), and then the LED 39 is turned or kept "on" (step S20), before returning to step S2.

In contrast, when it is determined NO at step S17, the processing at steps S14-S16 is executed by the CPU 30 as described above. To be specific, the electromagnetic valve 29 is made or kept "off" (step S14), the buzzer 15 is made or kept "off" (step S 15), and the LED 39 is made or kept "off" (step S16).

Accordingly, through the foregoing processing conducted by the CPU 30, the control signal supplied to the electromagnetic valve 29 is kept "off," when either the first or second switch 18 or 19 is turned "on" solely. The electromagnetic valve 29 thus keeps its closed valve state, which keeps the clutched states of the fluid clutches 28a, 28b, 28c and 28d. Since the joints 13a, 13b and 13c are positionally kept locked (clutched), the polyarticular arm 12 is also positionally kept locked, so that the endoscope 17 is positionally fixed (i.e. the position-fixed state).

In addition, during the position-fixed state being kept, the system is able to cope with an operator's operation that only either the first or second switch 18 or 19 is turned "on" and the "on" state lasts for a predetermined period of time (in the present embodiment, three seconds). Even if such an operation is carried out, the foregoing locked state of the polyarticular arm 12 is kept, while the buzzer 38 honks and the LED 39 flashes. Thus the operator is able to steadily know that the medical-device holding apparatus has failed to release its locked state (i.e., position-fixed state), which requires succeeding necessary operations such as unlocking re-operation. Hence the operator's operation can be smoothened.

Additionally, in cases where the endoscope 17 or polyarticular arm 12 is moved to rotate during a surgical operation, it may happen that the drape is pulled to accidentally push either the first or second switch 18 or 19. It may also happen that such a rotary operation involves an interference with other devices which may cause only either the first or second switch 18 or 19 to be turned "on" by mistake. Even such situations are caused, the foregoing information means immediately informs the operator of the currently operated state, thereby alleviating the operator from anxiety that the operator should take care of operations at all times. This reduces an operator's burden on the operations.

By the way, the exemplified processing shown in FIG. 5, which is executed by the CPU 30, can further be modified with regard to, for example, the order of on/off determinations for the first and second switches 18 and 19. The second switch 19 may be subjected to the on/off determination, before that for the first switch 18. With regard to the buzzer 38 and LED 39 serving as the information means, only one of the buzzer 38 and LED 39 may be employed.

Further, a period of time to be measured by the timer at step S17 cannot always be limited to 3 seconds, but may be a minimum period of time which can sense steadily the state in which "either the first or second switch 18 or 19 is "on"-operated alone. In other words, such a period of time can be defined as a time interval for measuring simultaneity for operator's operations. Hence, for example, an appropriately selected period of time, such as 1 second, 2 seconds, or 4 seconds, can be adopted, depending on design conditions or other necessary factors.

Moreover, as described, in the processing shown in FIG. 5 conducted by the CPU 30, the detection is made to recognize the state both the first and second switches 18 and 19 are operated "on" and a span of time from the "on" operation at one switch 18 (19) to that at the other switch 19 (18) is within a predetermined period of time. This manner of detection can be applied to detection of malfunctioning states of either the first or second switch 18 or 19. For example, in cases where either switch is in fault condition due to a fusion-bonded switch contact, the processing shown in FIG. 5 can also be used for detecting the malfunction. In order to achieve this, the CPU 30 is set to execute the processing shown in FIG. 5 at specific intervals (for example, at intervals of a few minutes or at a time when the apparatus is activated). Hence, when either the first or second switch 18 or 19 is out of order (in other words, no operation is made but the switch is in the "on" state), this state is detected, resulting in that the buzzer 38 honks and the LED 39 flashes. Using an LED dedicated to this detection, which is different from the LED 39 designated as means to inform the foregoing improperly operated states or accidentally operated states, makes it easier for an operator to immediately recognize the malfunctioning states of the various switches. In this case, of course, either one of the buzzer and LED can be used as informing means.

Moreover, signals to be detected at steps S1, S2 and S7 in FIG. 5 are not be limited to signals from the first and second switches 18 and 19, but may be signals from electric circuits electrically connected to these switches, respectively. For instance, in a configuration where a relay is arranged to each of the first and second switches 18 and 19 to provide a switch signal via each relay, a signal outputted from each relay can be an object to be detected. Thus, the object to be detected can be developed to peripheral circuits of the switches, such as relay whose contact is fusion-bonded, which may not be confined to the detection of malfunction of the switch itself. This way of detection can raise reliability for the arm-move prohibiting control.

Second Embodiment

Figure 6:
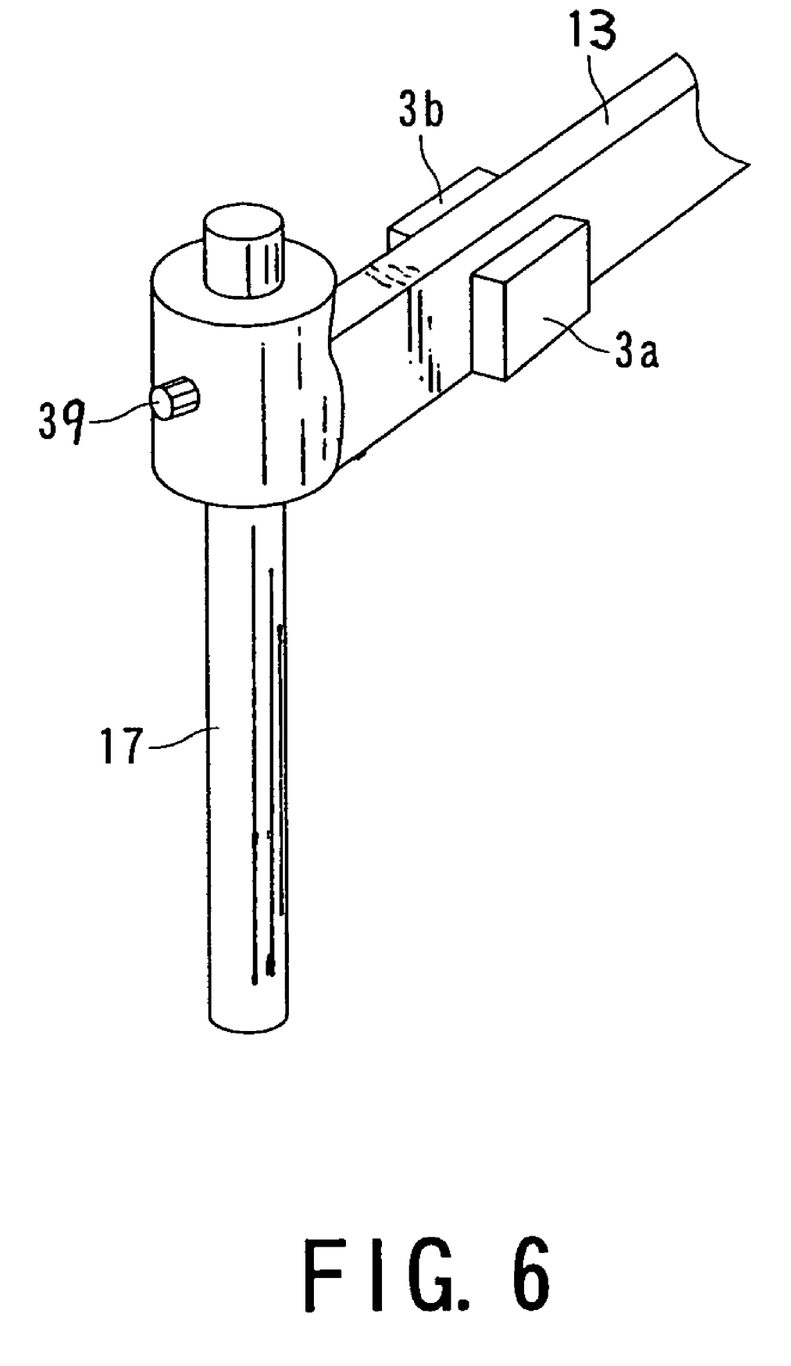
FIG. 6 is a perspective view showing a holder employed by a medical-device holding apparatus in a second embodiment according to the present invention.
Figure 7:
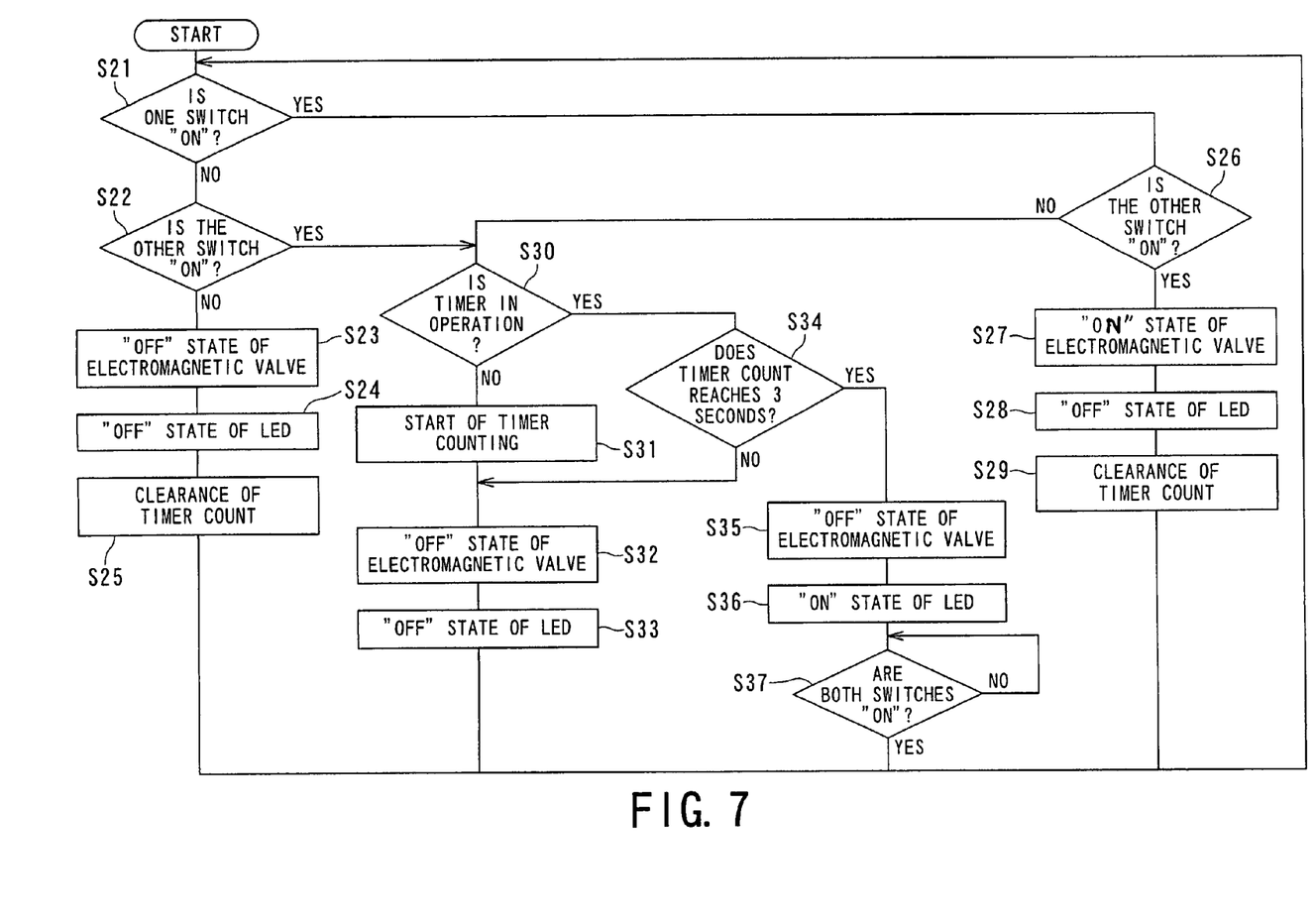
FIG. 7 is a flowchart showing the operations performed by a controller in the second embodiment.

Referring to FIGS. 6 and 7, a second embodiment of the medical-device holding apparatus according to the present invention will now be described. In the second and subsequent embodiments, the configuration elements identical or similar to those in the first embodiment will be referred by the same reference numerals for the sake of simplified or omitted explanations.

The configurations in the second embodiment differ from those in the first embodiment in the shape of the holder 13 and the locations of the first and second switches disposed in the holder 13. In addition, a further difference from the first embodiment is how to escape from a locked state where the joints are locked due to the fact that either the first or second switch is alone operated for a predetermined period of time or more.

As shown in FIG. 6, in order that the fluid clutches in the joints of the polyarticular arm 12 (arms 12a-12c) have clutched and unclutched in a selective manner, there are provided two operation switches 3a and 3b mounted on the holder 13 handled for moving the endoscope 17. The two operation switches 3a and 3b are arranged on both sides of the plate-like holder 13 in such a manner that they are located at the same position in the longitudinal direction of the holder 13. The LED 39 is mounted on the endoscope-side tip of the holder 13. Incidentally, in the present embodiment, the buzzer is omitted from being arranged. When an operator such as surgeon holds grips the holder 13 to press the two operation switches 3a and 3b by the thumb and first finger at the same time (simultaneously or almost simultaneously), the fluid clutches operates to release the fixed state of each joint (i.e., unclutched). Thus as long as the two operation switches 3a and 3b are not pressed at the same time or within a predetermined period of time, each joint will not be from its clutched state.

In this medical-device holding apparatus, it may happen that rotating the endoscope 17 or arms 12a-12c during a surgical operation causes the drape to be tightened or an interference with other equipments, so that the operation switches 3a and 3b are pressed by mistake. To prevent such situations, the CPU 30 executes the processing according to the flowchart shown in FIG. 7.

That is, at step S21 in FIG. 7, it is determined whether or not one operation switch 3a, of the two operation switches 3a and 3b, is in "on." When this determination shows NO, the processing is shifted to step S22, where the other operation switch 3b is subjected to the determination whether or not it is made "on." If the determination at step S22 is NO, the processing goes to step S23 to turn or keep the electromagnetic valve 29 "off." Further, the processing is performed at step S24 to turn or keep the LED 39 "off" and, at step S25, to initialize the timer BT, before returning to step S21.

Meanwhile when it is determined YES at step S21, the processing is shifted to step S26, where the determination switch 3b is subjected to the determination whether or not it is made "on." The determination of YES allows the processing to be performed at step S27, where the electromagnetic valve 29 is made or kept "on." Then at step S28, the LED 39 is made or kept "off," and at step S29, the timer BT is initialized, before being shifted to step S21.

In the case of the determination of YES at step S22 or NO at step S26, the processing is shifted to step S30, where it is determined whether or not the timer BT is in operation. If the determination is NO (not in operation), the processing at steps S31 to S33 is carried out in sequence. The timer BT is started to count the time (step S31), the electromagnetic valve 29 is kept "off" (step S32), and the LED 39 is kept "off" (step S33). Then the processing is made to return to step S21.

On the other hand, if it is determined "YES" at step S30, that is, it is found that the timer BT is in operation, the processing is shifted to step S34 to further determine whether or not the count of the timer BT shows three seconds (i.e., a predetermined period of time) or more. If the determination at step S34 is YES, i.e., a period of 3 seconds or more is counted, the processing is carried out such that the electromagnetic valve 29 is in its "off" state (step S35) and the LED 39 is turned "on" (step S36). The processing is then shifted to step S37 to determine whether or not the operation switches 3a and 3b both are in their "off" states. If this determination is NO, this termination processing is repeated to wait for a situation where the operation switches 3a and 3b both become "off." When both the switches 3a and 3b are released from being pushed (the determination at step S37 is YES), the processing escapes from the repeated determinations at step S37. The CPU 30 returns the processing to step S21.

When the determination at step S34 is NO (i.e. a predetermined period of 3 seconds or more has yet to come), the processing at steps S32 and S33 is performed as described before.

As a result of the foregoing processing, when either one of the operation switches 3a and 3b attached to the holder 13 is made "on" and its "on" state lasts for the predetermined period of time (e.g., 3 seconds in the present embodiment, but not limited to this period of time), the electromagnetic valve 29 becomes "off." The arms 12a-12c are therefore locked to not allow any moves thereof. At the same time, the LED 39 is turned "on" to notify the surgeon (i.e., operator) that the current operation toward the switches is improper. This locked state can be released only when the switches 3a and 3b both are made "off," thanks to the processing at step S37 in FIG. 7.

Third Embodiment

Figure 8:
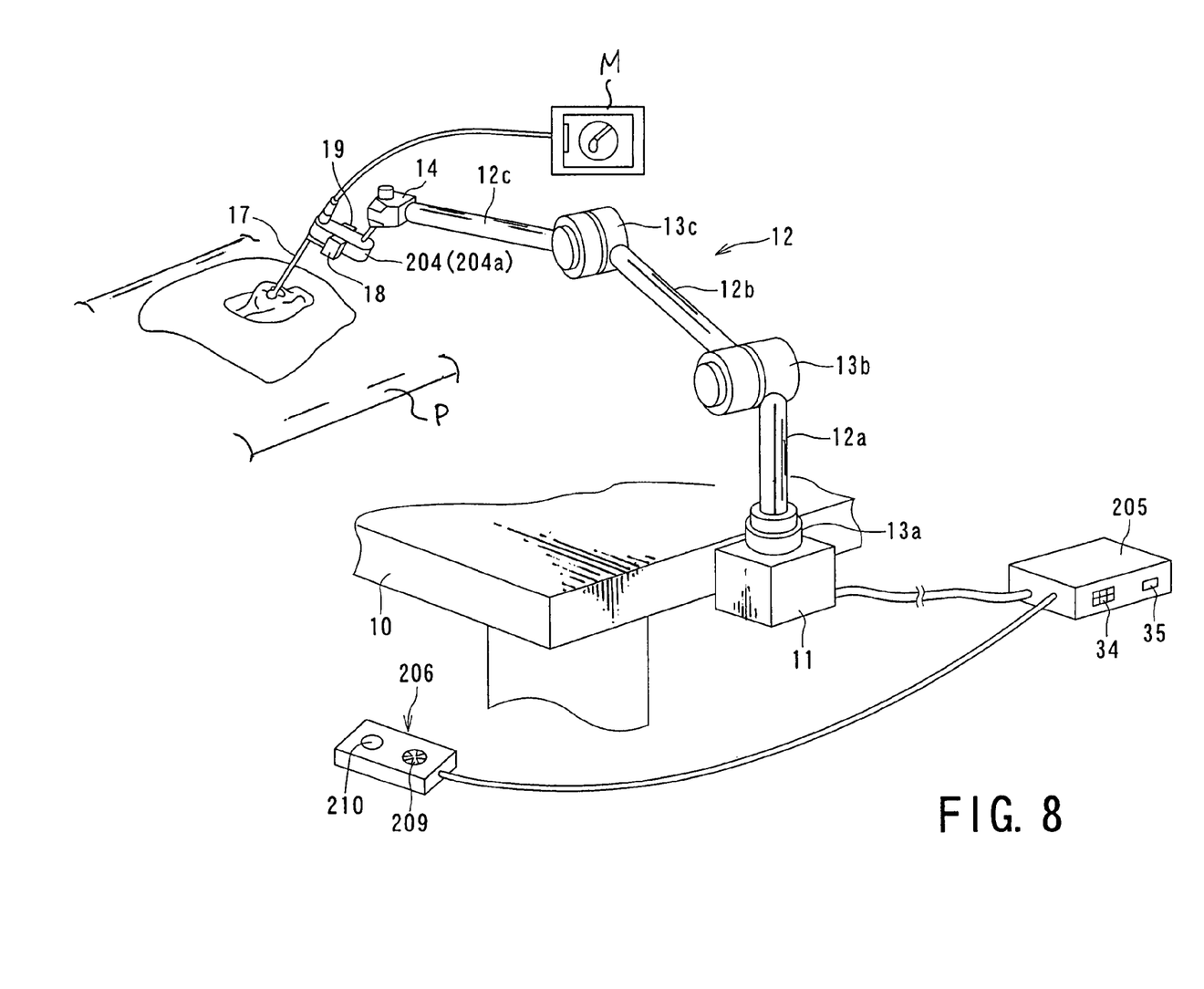
FIG. 8 is a perspective view showing a medical-device holding apparatus in a third embodiment according to the present invention.
Figure 9:
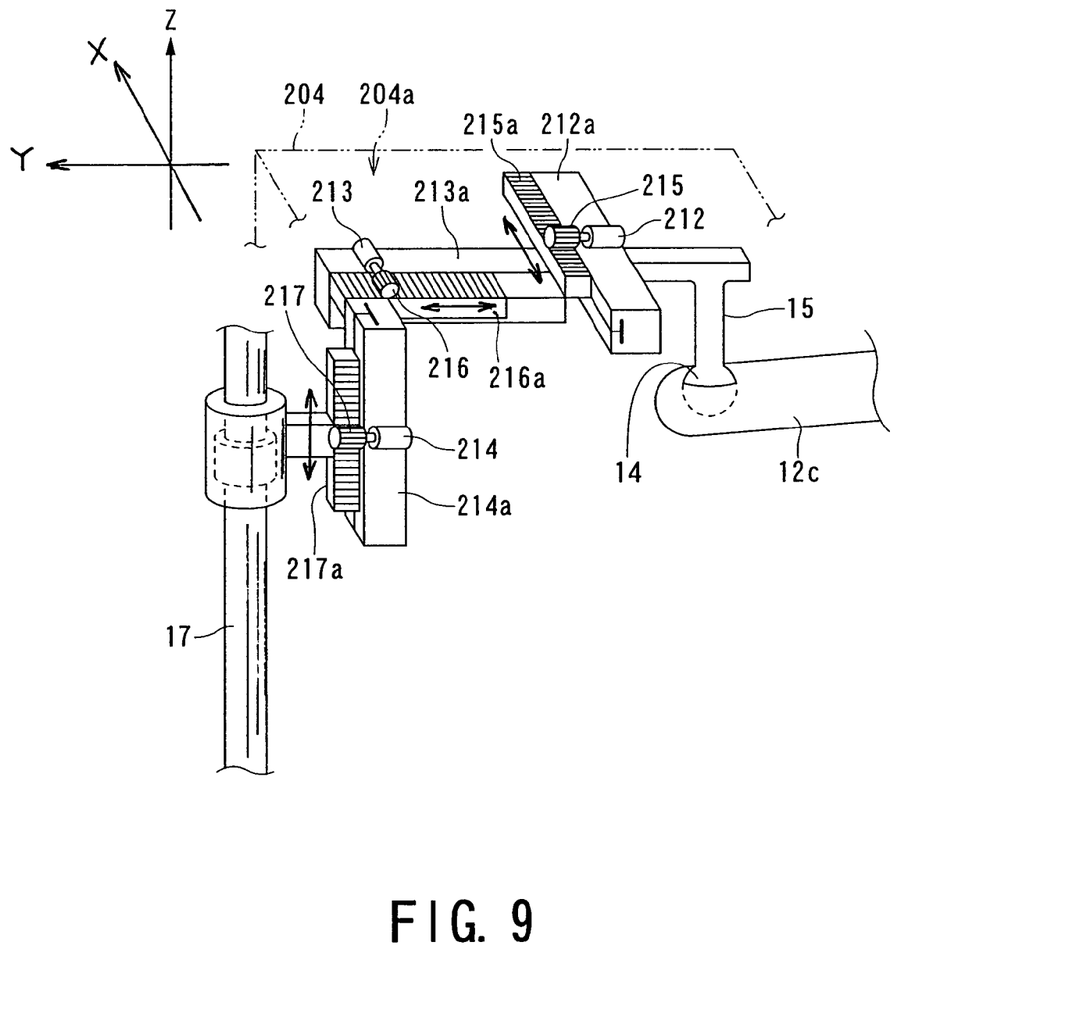
FIG. 9 shows a block diagram of an electric field-of-view driver according to the third embodiment.
Figure 10:
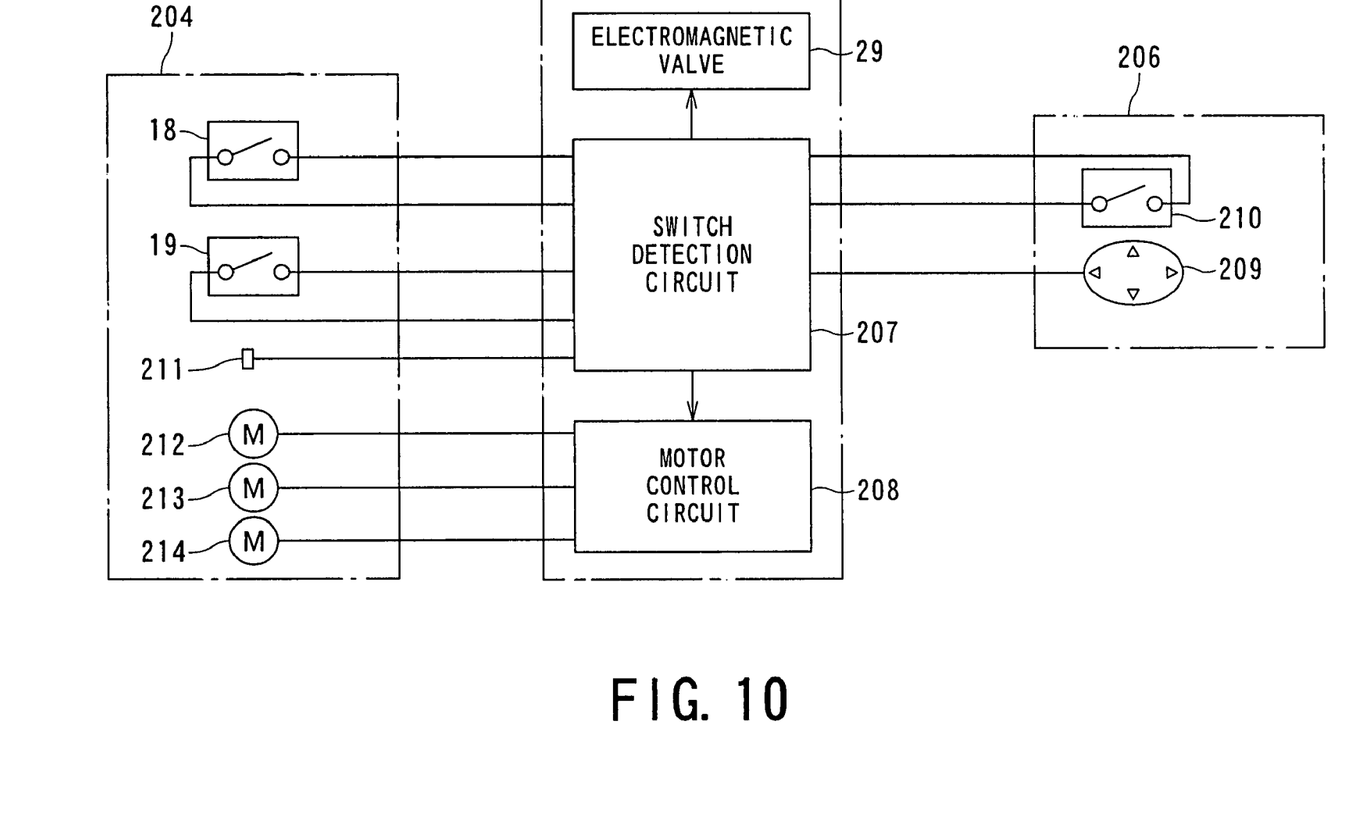
FIG. 10 illustrates a block diagram of a control circuit according to the third embodiment.

Referring to FIGS. 8-10, a third embodiment of the medical-device holding apparatus according to the present invention will now be described.

As shown in FIG. 8, a holder 204, which holds endoscope 17, is attached to the head-side arm 12a via the ball joint 14. To the holder 204 is attached an electric view-change driver 204a which will be described later, which is in charge of changing an observing direction of the endoscope 17 by selectively moving it in the X-axis, Y-axis and Z-axis directions. The electric view-change driver 204a is eclectically connected to a foot switch box 206 via a control box 205.

Using FIGS. 9 and 10, the holder 204, control box 205, and foot switch box 206 will now be described.

The control box 205 is provided with, in addition to the foregoing electromagnetic valve 29, a switch detection circuit 207 and a motor control circuit 208, wherein the switch detection circuit 207 is electrically connected to the electromagnetic valve 29. Additionally, electrically connected to the switch detection circuit 207 are a joystick switch 209 and a drive switch 210, which are equipped in the footswitch box 206. The joystick switch 209 is provided with a four-way switch which operates to move the endoscope 17 in the upward, downward, and lateral directions. By way of example, the switch detection circuit 207 is functionally configured with the aid of the software processing carried out by a CPU, like the foregoing control box in the first embodiment.

The holder 204 is provided with the foregoing first and second switches 18 and 19 and an LED 211, which are electrically connected with the switch detection circuit 207. The holder 204 is also provided with an X-axis motor 212, Y-axis motor 213, and Z-axis motor 214, which are all electrically coupled with the motor control circuit 208. Operator's operations at the joystick switch 209 allow the motor control circuit 208 to drive the X-, Y- and Z-axes motors 212, 213 and 214 mounted in the holder 204 concurrently or selectively so that the view of the endoscope 17 can be moved in a controlled manner.

The electric view-change driver 204a is structured as schematically shown in FIG. 9, in which there are provided with an X-axis housing 212a, Y-axis housing 213a, Z-axis housing 214a. The X-axis housing 212a is arranged to engage with an X-axis motor 212 with a motor shaft having a pinion gear 215 at one end thereof. This pinion gear 215 is engaged with an X-axis rack 215a slidably formed on the X-axis housing 212a in the X-axis direction.

The Y-axis housing 213a is mounted on the X-axis rack 215a. The Y-axis housing 213a is arranged to engage with a Y-axis motor 213 with a motor shaft having a pinion gear 216 at one end thereof. This pinion gear 216 is engaged with a Y-axis rack 216a slidably formed on the Y-axis housing 213a in the Y-axis direction.

Moreover, the Z-axis housing 214a is mounted on the Y-axis rack 216a. The Z-axis housing 214a is arranged to engage with a Z-axis motor 214 with a motor shaft having a pinion gear 217 at one end thereof. This pinion gear 217 is engaged with a Z-axis rack 217a slidably formed on the Z-axis housing 214a in the Z-axis direction. This Z-axis rack 217a finally holds the endoscope 17, as illustrated in FIG. 9.

Thus, a surgeon (operator) can grip the holder 204 to push down the first and second switches 18 and 19, for example, by the thumb and first finger at the same tame or within a predetermined period of time. This push activates, with the aid of the switch detection circuit 207, the electromagnetic valve 29 to release the fluid clutch of each joint from being clutched. In contradiction to this, in the remaining cases where the first and second switches 18 and 19 are not pushed down at the same time or within the predetermined period of time, unlike the above, the switch detection circuit 207 will not permit each joint to be released from being fixed. Of course, when only one of the two switches 18 and 19 is continuously made "on" the predetermined period of time (e.g., 3 seconds) or more, the switch detection circuit 207 will issue a signal to light up the LED 211 in order to inform the operator about the improper operation, which is similar to that in the second embodiment.

This control for the operator's operations at the two switches 18 and 19 may be realized in the same or similar way as or to the processing based on the flowchart shown in FIG. 5 or 7, which can be assigned to the control box 205.

The joystick switch 209 on the footswitch box 206 is operated to decide a direction, information indicative of the decided information being displayed on a monitor M as shown in FIG. 8. After the decision of this direction, the drive switch 210 is turned "on," so that the electric view-change driver 204a is driven in response to this instruction. And as long as the joystick switch 209 is operated within a predetermined period of time (for example, 5 seconds) starting from the switch "on" of the drive switch 210, that is, both the switches 209 and 210 are operated ("on") within the predetermined period of time in the similar manner to the forgoing, the switch detection circuit 207 and motor control circuit 208 jointly operate to instruct the electric view-change driver 204a to drive the X-, Y- and Z-axis motors 212, 213 and 214.

However, in the case that only either one of the joystick switch 209 and drive switch 210 is operated ("on") continuously the predetermined period of time or more, a signal from the switch detection circuit 207 will cause the LED 211 to light to inform an operator of this improper operation. Concurrently, the X-, Y- and Z-axes motors 212-214 in the electric view-change driver 204a are locked not to be driven, whereby the view will be prohibited from being changed.

This control for the operator's operations at both the joystick switch 209 and the drive switch 210 can also be performed in the same manners as above based on based on the flowchart shown in FIG. 5 or 7, which can be assigned to the control box 205.

(Modifications)

Figure 11:
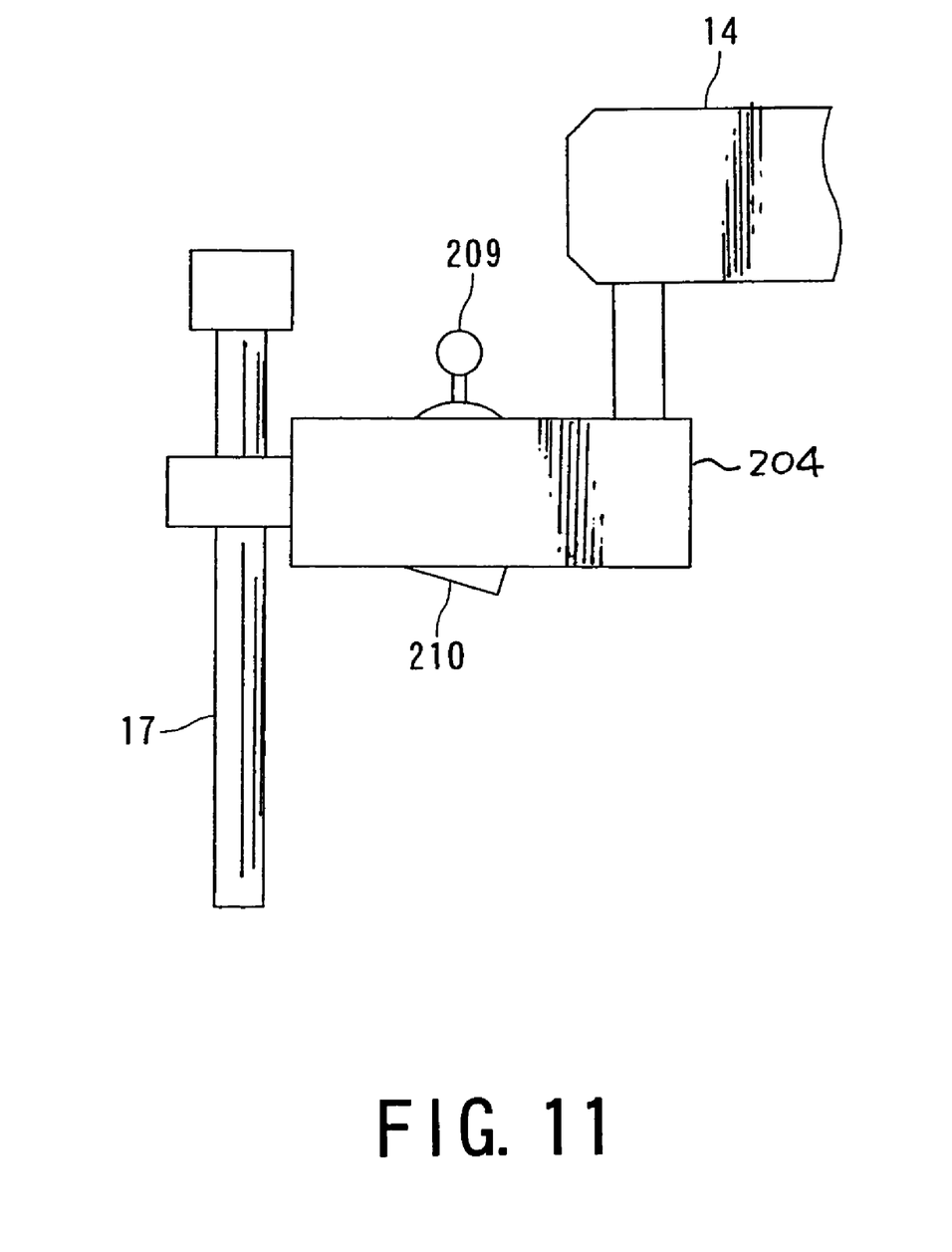
FIG. 11 is a perspective view indicating a holder adopted by a medical-device holding apparatus according to a modification directed to the third embodiment.

FIG. 11 shows a modification of the third embodiment, wherein the holder 204 is provided with both the joystick switch 209 and drive switch 210. Hence an operator can grip the holder 204, during which time the operator operates both the switches 209 and 210. In this modification, there is no necessity of employing the footswitch box 206, thus simplifying the switch constructions.

In addition, though the foregoing various embodiments have been described about the construction in which the endoscope serving as the medical device is employed, however, this is not a definitive list. Any other types of medical treatment devices can be used as a medical device, so that the similar advantages to the foregoing can be provided.

In each of the foregoing embodiments, the polyarticular arm consisting of three joints has been described, but the number of joints is not confined to three. The polyarticular arm having a desired number of joints can be applied to the present invention to enjoy the foregoing advantages which are characteristic of the present invention.

Although the description above contains many specificities, these should not be construed as limiting the scope of the invention but as merely providing illustrations of some of the presently preferred embodiments of the present invention. Thus the scope of the present invention should be determined by the appended claims. For example, in the third embodiment, the control for locking the electric view-change driver may be reduced in practice solely, separately from the control for lock and unlocking the polyarticular arm.

What is claimed is:

1. An apparatus for holding a medical device, comprising:
   an arm unit spatially movable for spatially moving the medical device;
   an operation unit configured to be manually gripped by an operator for moving the arm unit, mechanically connected to both the arm unit and the medical device such that movement of the operation unit by the operator produces movements of both the arm unit and the medical device, and equipped with a plurality of switches to be operated by a hand of the operator which hand grips the operation unit when the medical device requires to be moved spatially;

a determination unit configured to determine whether or not there is provided a predetermined switch operated state where the plurality of switches are operated within a predetermined period of time starting from a time instant at which one of the plurality of switches is first operated; and a movement controller configured to prohibit the arm unit from moving spatially even when the operator manually operates the switches, unless the determination unit determines that the predetermined switch operated state has been provided;

an informing device informing the operator of a state where the arm unit has been prohibited from being moved even if the plurality of switches were operated; and an informing controller controlling the informing device to inform the operator of the prohibited state in cases where the movement controller has prohibited the arm unit from being moved.

2. The apparatus according to claim 1, wherein the operation unit is equipped a holder being gripped by the operator and having both ends, one end of the holder connected to part of the arm unit and the other end of the holder holding the medical device.

3. The apparatus according to claim 2, wherein
the arm unit is equipped with an arm having both ends one of which is secured to a fixed portion, having joints being partly arranged in the arm, having brakes placed in the joints so as to be unlocked when the predetermined switch operated state has been provided, and selectively enabling the brakes to be locked or unlocked in response to a control signal,
the plurality of switches are arranged to the holder and are configured to selectively command the brakes in the joints to be locked or unlocked;
the determination unit is adapted to determine the predetermined switch operated state which differs from an improperly operated state of the plurality of switches; and
the movement controller is adapted to prohibit the brakes from being unlocked unless the determination unit determines that the predetermined switch operated state has been provided.

4. The apparatus according to claim 3, wherein the arm unit is a polyarticular arm with the joints which are plural in number.

5. The apparatus according to claim 4, wherein the medical device is an endoscope.

6. The apparatus according to claim 3, wherein the plurality of switches include a first switch and a second switch which are operated by the operator in one hand for moving the arm unit, and
the predetermined switch operated state is a state where one of the first and second switches is first operated and the other is then operated within the predetermined period of time starting from a time instant when the one of the first and second switches is operated.

7. The apparatus according to claim 6, wherein the first and second switches are equipped with switch operating portions, respectively, with which the operator operates.

8. The apparatus according to claim 7, wherein the holder has two surfaces mutually opposed and the first switch and the second switch are disposed so that the switch operating portions of the first and second switches are located on the two mutually opposed surfaces of the holder, respectively.

9. The apparatus according to claim 6, comprising
an informing device informing the operator of a state where the arm unit has been prohibited from being moved even if the first and second switches were operated; and
an informing controller informing the operator of the prohibited state using the information device in cases where the movement controller has prohibited the arm unit from being moved.

10. The apparatus according to claim 9, wherein the informing device is at least one of a light generating device and a sound generating device.

11. The apparatus according to claim 10, wherein the light generating device is an LED (light emitting diode) and the sound generating device is a buzzer.

12. The apparatus according to claim 3, wherein each of the plurality of switches is equipped with a switch operating portion with which the operator operates by hand and the plurality of switches are secured to the holder gripped by the operator when the operator operates the medical device.

13. The apparatus according to claim 12, wherein the holder has two surfaces mutually opposed and the plurality of switches include a first switch and a second switch, the first and second switches having switch operating portions, respectively, and being disposed so that the switch operating portions of the first and second switches are located on the two mutually opposed surfaces of the holder, respectively.

14. The apparatus according to claim 13, wherein each of the first and second switches is a microswitch with a switch lever serving as the switch operating portion.

15. The apparatus according to claim 1, wherein the plurality of switches include a first switch and a second switch which are operated by the operator in one hand for moving the arm unit, and
the predetermined switch operated state is a state where one of the first and second switches is first operated and the other is then operated within the predetermined period of time starting from a time instant at which the one of the first and second switches is operated.

16. The apparatus according to claim 1, wherein the arm unit is equipped with a polyarticular arm having a plurality of joints enabling the polyarticular arm from moving spatially.

17. The apparatus according to claim 1, wherein the medical device is an endoscope.

18. The apparatus according to claim 1, wherein the informing device is at least one of a light generating device and a sound generating device.

19. The apparatus according to claim 18, wherein the light generating device is an LED (light emitting diode) and the sound generating device is a buzzer.

20. The apparatus according to claim 1, wherein the predetermined switch operated state is a state which differ from a malfunctioning state of the operation unit and an accidentally operated state of the plurality of switches.

21. An apparatus for holding a medical device, comprising:
an arm unit spatially movable for spatially moving the medical device;
operation means configured to be manually handled by an operator for moving the arm unit, mechanically connected to both the arm unit and the medical device such that movement of the operation unit by the operator produces movements of both the arm unit and the medical device, and equipped with a plurality of switches to be operated a hand of by the operator which hand grips the operation unit when the medical device requires to be moved spatially;

determination means configured to determine whether or not there is provided a predetermined switch operated state where the plurality of switches are operated within a predetermined period of time starting from a time instant at which one of the plurality of switches is first operated; and movement control means configured to prohibit the arm unit from moving spatially even when the operator manually operates the switches, unless the determination means determines that the predetermined switch operated state has been provided;

an informing device informing the operator of a state where the arm unit has been prohibited from being moved even if the plurality of switches were operated; and an informing controller controlling the informing device to inform the operator of the prohibited state in cases where the movement controller has prohibited the arm unit from being moved.

22. The apparatus according to claim 21, comprising
an informing device informing the operator of a state where the arm unit has been prohibited from being moved even if the plurality of switches were operated; and an informing controller informing the operator of the prohibited state using the information device in cases where the movement controller has prohibited the arm unit from being moved.

23. An apparatus for holding a medical device, comprising:
an arm unit spatially movable for spatially moving the medical device;

an electric driver, secured to the arm unit, driving the arm unit for spatially moving the medical device;

operation means manually operable by an operator for moving the arm unit, mechanically connected to both the arm unit and the medical device such that a movement of the operation unit by the operator leads to movements of both the arm unit and the medical device, and equipped with a plurality of switches to be operated by a hand of the operator which hand grips the operation unit when the medical device requires to be moved spatially;

determination means determining whether or not there is provided a predetermined switch operated state where all the plurality of switches are operated within a predetermined period of time starting from a time instant at which one of the plurality of switches is first operated; and electric-operation control means prohibiting the electric driver from driving the arm unit even when the operator manually operates the switches, unless the determination means determines that the predetermined switch operated state has been provided; an informing device that informs the operator of a state where the arm unit has been prohibited from being moved even if the plurality of switches were operated; and an informing controller informing the operator of the prohibited state using the information device in cases where the movement controller has prohibited the arm unit from being moved.

24. A method for controlling spatial movement of a medical device, the medical device being mechanically held by an operation unit mechanically connected to an arm unit by allowing an operator to operate a plurality of switches secured to the operation unit, the operation unit being manually handled by the operator, a movement of the operation unit by the operator producing movements of both the arm unit and the medical device, the plurality of switches being operated by a hand of the operator, which hand grips the operation unit when the medical device requires to be moved spatially, the method comprising steps of:

determining whether or not there is provided a predetermined switch operated state where the plurality of switches are operated within a predetermined period of time starting from a time instant at which one of the plurality of switches is first operated; and prohibiting the arm unit from moving spatially even when the operator manually operates the switches, unless it is determined that the predetermined switch operated state has been provided; and informing the operator of a state where the arm unit has been prohibited from being moved even if the plurality of switches were operated; unless it is determined that the predetermined switch operated state has been provided.

25. The method according to claim 24, wherein the determination step determines the predetermined switch operated state by detecting a situation where one of the plurality of switches is first operated and a remaining one of the plurality of switches are then operated within the predetermined period of time starting from a time instant at which the one of the plurality of switches is first operated.

26. The method according to claim 25, comprising a step of informing the operator that the arm unit has been prohibited from being moved even if the plurality of switches were operated.

27. An apparatus for holding a medical device, comprising:
an arm unit spatially movable for spatially moving the medical device;

an operation unit manually operable by an operator for moving the arm unit, mechanically connected to both the arm unit and the medical device such that movement of the operation unit by the operator produces movements of both the arm unit and the medical device, and equipped with a plurality of switches to be operated by a hand of the operator which hand grips the operation unit when the medical device requires to be moved spatially;

a determination unit configured to allow determining whether or not there is provided a predetermined switch operated state where the plurality of switches are operated within a predetermined period of time starting from a time instant at which one of the plurality of switches is first operated; and an informing device responsive to the operator's manual operations of the plurality of switches by informing the operator of a switch improperly operated state where it is not determined by the determining unit that the predetermined switch operated state has been provided; and an informing controller controlling the informing device to inform the operator of the switch improperly operated state.

28. The apparatus according to claim 2, wherein the determination unit determines whether or not there is provided the predetermined switch operated state where one of the plurality of switches is first operated and the remaining switch is then operated within the predetermined period of time starting from a time instant at which the one of the plurality of switches is first operated.

* * * * *